(12) United States Patent
Matsumoto et al.

(10) Patent No.: US 11,771,678 B2
(45) Date of Patent: Oct. 3, 2023

(54) THERAPEUTIC AGENT FOR NEUROPATHY IN ORGANIC ACIDEMIA OF WHICH MECHANISM RELIES ON INCREASE IN CAMP

(71) Applicant: NATIONAL UNIVERSITY CORPORATION KUMAMOTO UNIVERSITY, Kumamoto (JP)

(72) Inventors: Shiro Matsumoto, Kumamoto (JP); Takumi Era, Kumamoto (JP); Fumio Endo, Kumamoto (JP)

(73) Assignee: NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 17/198,904

(22) Filed: Mar. 11, 2021

(65) Prior Publication Data

US 2021/0260020 A1  Aug. 26, 2021

Related U.S. Application Data

(63) Continuation of application No. 16/341,321, filed as application No. PCT/JP2017/037507 on Oct. 17, 2017, now abandoned.

(30) Foreign Application Priority Data

Oct. 17, 2016 (JP) .................. 2016-203955

(51) Int. Cl.
| | |
|---|---|
| A61K 31/352 | (2006.01) |
| A61K 31/137 | (2006.01) |
| A61K 31/196 | (2006.01) |
| A61K 31/455 | (2006.01) |
| A61K 31/52 | (2006.01) |
| A61K 31/55 | (2006.01) |
| A61K 31/7076 | (2006.01) |

(52) U.S. Cl.
CPC .......... *A61K 31/352* (2013.01); *A61K 31/137* (2013.01); *A61K 31/196* (2013.01); *A61K 31/455* (2013.01); *A61K 31/52* (2013.01); *A61K 31/55* (2013.01); *A61K 31/7076* (2013.01)

(58) Field of Classification Search
CPC .......... A61P 25/00; A61P 3/00; A61K 31/455
See application file for complete search history.

(56) References Cited

U.S. PATENT DOCUMENTS

| | | |
|---|---|---|
| 2005/0009742 A1 | 1/2005 | Bertilsson et al. |
| 2005/0009847 A1 | 1/2005 | Bertilsson et al. |
| 2005/0209142 A1 | 9/2005 | Bertilsson et al. |
| 2006/0079448 A1 | 4/2006 | Bertilsson et al. |
| 2009/0156496 A1 * | 6/2009 | Benowitz .................. A61P 3/10 514/6.9 |
| 2009/0232775 A1 | 9/2009 | Bertilsson et al. |

FOREIGN PATENT DOCUMENTS

| | | |
|---|---|---|
| JP | 2006-514630 A | 5/2006 |
| JP | 2009-536950 A | 10/2009 |
| WO | 2004/045592 A2 | 6/2004 |
| WO | 2007/133749 A2 | 11/2007 |

OTHER PUBLICATIONS

Kavirajan et al., Lancet Neurol 2007, 6, 782-92.*
Vattakatuchery et al., World Journal of Psychiatry; 2013, 3(3), 62-64.*
International Search Report dated Jan. 23, 2018 filed in PCT/JP2017/037507.
Loureiro, S. O. et al., "Propionic and methylmalonic acids increase cAMP levels in slices of cerebral cortex of young rats via adrenergic and glutamatergic mechanisms", Biochim. Biophys. Acta, Jun. 10, 2005, vol. 1740, No. 5, pp. 460-466.; Cited in ISR; English Text.
De Mattos-Dutra, A. et al., "Propionic and methylmalonic acids inhibit the in vitro phosphorylation of 85 kDa cytoskeletal protein from cerebral cortex of rats", Neurochem. Int., Nov. 2, 1998, vol. 33, No. 5, pp. 407-414.; Cited in ISR; English Text.
Kavirajan et al., Lancet Neural 2007, 6, 782-92; Cited in USPTO office communication dated Dec. 14, 2020 issued for U.S. Appl. No. 16/341,321.
Vattakatuchery et al., World Journal of Psychiatry; 2013, 3(3), 62-64; Cited in USPTO office communication dated Dec. 14, 2020 issued for U.S. Appl. No. 16/341,321.

* cited by examiner

*Primary Examiner* — Pancham Bakshi
(74) *Attorney, Agent, or Firm* — Rankin, Hill & Clark LLP

(57) ABSTRACT

[Object] To clarify the mechanism associated with neuropathy in methylmalonic acidemia and to develop a new therapeutic drug or the like for neuropathy in organic acidemia on the basis of this finding.

[Solving Means] The inventors established technologies for the establishment of iPS cells derived from a methylmalonic acidemia patient and establishment of a stable maintenance and culturing method using peripheral blood lymphocytes of a methylmalonic acidemia patient, and for the differentiation of methylmalonic acidemia patient-derived iPS cells into nerve cells. The inventors made clear that neuropathy in organic acidemia can be treated and prevented by replenishing cAMP using a series of these experiment technologies. The drug of the invention treats or prevents neuropathy by increasing cAMP in organic acidemia.

4 Claims, 5 Drawing Sheets

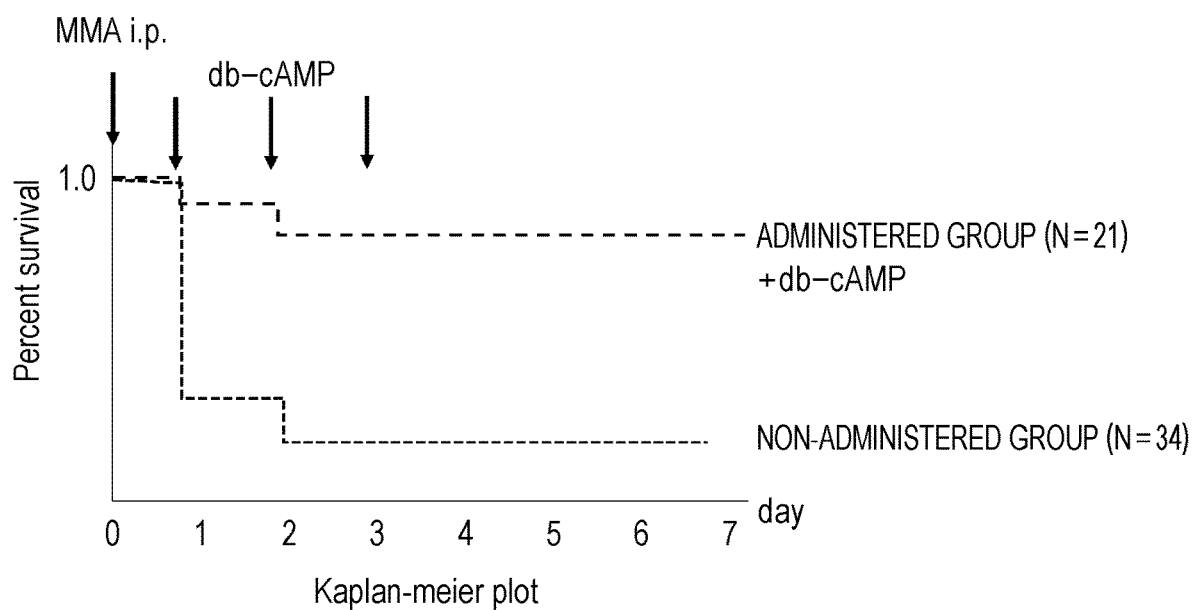

THERAPEUTIC AGENT FOR NEUROPATHY IN ORGANIC ACIDEMIA OF WHICH MECHANISM RELIES ON INCREASE IN CAMP

TECHNICAL FIELD

The present invention relates to a therapeutic agent for neuropathy in organic acidemia of which mechanism relies on an increase in cAMP.

BACKGROUND ART

Organic acidemia is a disease in which organic acids accumulate excessively in the living body due to abnormality in metabolizing enzymes. In organic acidemia, due to excessive accumulation of organic acids, metabolic acidosis, hyperammonemia, hypoglycemia, and the like occur, and as the results of these, respiration disorder or consciousness disorder develop in an acute stage, and symptoms such as anorexia and vomiting develop in a chronic stage. Furthermore, organic acidemia is also known such that curative remedy is difficult, and the fatality rate is high.

Examples of the treatment method for organic acidemia include dietetic therapy, pharmacotherapy, dialysis, and implantation.

Dietetic therapy is a method of treatment in which meals with limited proteins and amino acids such as isoleucine, valine, and methionine, which may be causative substances for organic acid metabolites are taken. Dietetic therapy enables suppression of accumulation of organic acids, which are causative of organic acidemia; however, dietetic therapy is not capable of completely preventing this accumulation. Therefore, it is an effective method of treatment carried out for the purpose of stabilizing symptoms in a chronic stage; however, dietetic therapy is not a curative remedy.

Meanwhile, in regard to pharmacotherapy, arginine and CARBAGLU that detoxify ammonia, and carnitine hydrochloride that binds to organic acids and accelerates excretion, are used. Pharmacotherapy is a method of treatment used not only in a chronic stage but also at the time of aggravation of symptoms in an acute stage. Furthermore, pharmacotherapy is carried out together with hemodialysis in many cases, for the purpose of eliminating organic acids from the blood. Both of these pharmacotherapy and dialysis are capable of rapid elimination of organic acids at the time of aggravation of symptoms; however, since they do not enable complete exclusion of the accumulation of causative organic acids, these pharmacotherapy and dialysis are not curative remedies.

Compared to these, liver transplantation has been carried out as the only life supporting method for organic acidemia. Furthermore, since it has been made obvious that when only liver transplantation is carried out, neurological symptoms progress slowly, and neurological aftereffects and renal disorder come as complications at a high rate, recently, renal and liver co-transplantation of performing liver transplantation and renal transplantation at the same time is carried out in overseas countries as an advanced treatment.

As a result of enhancement of these transplantation treatment and dialysis technologies, the treatment outcome for organic acidemia has been improved, and the fatality rate has been certainly decreased. However, even with regard to this renal and liver co-transplantation, it has been reported that the organic acid concentration in the cerebrospinal fluid is not normalized, or severe neuropathy remains. That is, while the fatality rate is decreased by a transplantation treatment, since neuropathy is not completely cured in survival cases, neuropathy causes deterioration of the QOL of patients.

Under such circumstances, there is a strong demand for the development of methods of treatment for neuropathy in organic acidemia.

Meanwhile, cAMP is an intracellular signal transducer functioning as a second messenger in cells.

The existence, functions and the like of cAMP have been known for long; however, the relevance between cAMP and organic acidemia is not clearly known. On the other hand, with regard to cAMP and neuropathy, technologies suggesting this relevance are found here and there (Patent Documents 1 and 2).

CITATION LIST

Patent Document

Patent Document 1: WO 2004/045592 A
Patent Document 2: WO 2007/133749 A

SUMMARY OF THE INVENTION

Problem to be Solved by the Invention

In Patent Document 1, a technology related to a composition and a method for increasing neurogenesis is disclosed. Furthermore, in Patent Document 2, a technology related to a method for treating and preventing peripheral neuropathy, and the like is disclosed.

In regard to these related art technologies, regulation of cAMP, a cAMP modulator, and the like are disclosed, and these suggest the relevance between central nervous system damage or peripheral neuropathy and cAMP.

However, even for neuropathy, there may be a variety of causes for development thereof depending on the disease that brings this neuropathy, and in these related art technologies, development of neuropathy in organic acidemia is neither disclosed nor suggested. In addition, with regard to neuropathy of organic acidemia, it is the current situation that no treatment based on a mechanism involving cAMP regulation is carried out, and there is no effective therapeutic drug.

Under such circumstances, among organic acidemias, the inventors paid attention to methylmalonic acidemia, which exhibits particularly high fatality rate and is also associated with poor long-term prognosis, and initiated a study.

The causes of disease of methylmalonic acidemia are roughly classified into deficiency of methylmalonyl CoA mutase (MCM), which is an enzyme, that catalyzes the metabolism from methylmalonyl CoA to succinyl CoA, and metabolic disorder of vitamin B12 (cobalamin), which is a co-enzyme of MCM. It has been considered that due to such deficiency or metabolic disorder, propionyl CoA and methylmalonyl CoA accumulate in the mitochondria, the amount of methylmalonic acid derived from these is increased, thereby impairing cellular functions, and severe organopathies are brought about. However, the details of the mechanism have been not clearly understood.

Under such circumstances, it is an object of the invention to clarify the mechanism related to neuropathy in methylmalonic acidemia, and to develop a new therapeutic drug or the like for neuropathy in organic acidemia based on the findings thus obtained.

Means for Solving Problem

The inventors conducted a thorough study, and as the result, they found that in organic acidemias including methylmalonic acidemia, a decrease in the cAMP concentration in nerve cells is causative of neuropathy. Thus, the inventors completed inventions such as a drug for treating and preventing neuropathy in organic acidemia by replenishing cAMP, and the like.

That is, the inventors conducted an investigation by establishing iPS cells from peripheral blood lymphocytes of methylmalonic acidemia patients and differentiating these cells into nerve cells, and the inventors made clear of the following facts. From such facts, the inventors made clear that neuropathy in organic acidemia can be treated and prevented by replenishing cAMP.

(1) The inventors discovered six compounds that bring specific recovery from neuronopathy in nerve cells derived from methylmalonic acidemia.

(2) These six compounds all have a common action of increasing intracellular cAMP or activating CREB, which is a downstream molecule.

(3) The cAMP concentration in nerve cells derived from methylmalonic acidemia was measured, and it was confirmed that the concentration was noticeably decreased compared to the concentration in nerve cells derived from a healthy person.

(4) Furthermore, since a decrease in the cAMP concentration was not seen in iPS cells derived from a methylmalonic acidemia patient, it was confirmed that this decrease in the cAMP concentration occurs as a result of differentiation into nerve cells in a methylmalonic acidemia patient.

(5) In regard to nerve cells derived from methylmalonic acidemia, it was found that when cAMP is added into the culture fluid, the cell viability and the mitochondrial function are restored to about 90% of those of nerve cells derived from a healthy person. A similar effect was also confirmed in propionic acidemia.

(6) It was confirmed that in nerve cells derived from methylmalonic acidemia, a decrease in cAMP is caused by a decrease in the activity of Adenylate cyclase. In addition, the activity of CREB that uses cAMP as a substrate is not inhibited, and when Adenylate cyclase-derived cAMP is supplemented, CREB is phosphorylated. Thus, it was confirmed that a therapeutic effect is exhibited on the basis of this phosphorylation as one of the mechanisms.

(7) In an in vivo model produced through administration of methylmalonic acid, an effect of suppressing the number of times and duration of seizure caused by convulsion and an effect of increasing the survival rate were confirmed, by administering a drug that supplements cAMP to the in vivo model.

The invention has the following configurations.

A first configuration of the invention is a therapeutic drug for neuropathy, intended for treating or preventing neuropathy by increasing cAMP in organic acidemia.

A second configuration of the invention is the therapeutic drug for neuropathy according to the first configuration, further intended for activating CREB.

A third configuration of the invention is the therapeutic drug for neuropathy according to the first or second configuration, in which the organic acidemia is an organic acidemia lowering the activity of Adenylate cyclase.

A fourth configuration of the invention is the therapeutic drug for neuropathy according to the first or second configuration, in which the organic acidemia is selected from any one or a plurality of methylmalonic acidemia and propionic acidemia.

A fifth configuration of the invention is the therapeutic drug for neuropathy according to any one of the first to fourth configurations, in which the increase in cAMP is achieved by any one of Forskolin, GW9508, NECA, SKF77434, nicotinamide, dobutamine, and db-cAMP.

A sixth configuration of the invention is the therapeutic drug for neuropathy according to the third configuration, in which the increase in cAMP is achieved by suppressing or preventing a decrease in the activity of Adenylate cyclase.

A seventh configuration of the invention is the therapeutic drug for neuropathy according to any one of the first to sixth configurations, in which a life prolongation effect is increased by treating or preventing neuropathy.

An eighth configuration of the invention is a method for treating or preventing neuropathy in organic acidemia by using the therapeutic drug for neuropathy according to any one of the first to seventh configuration.

Effect of the Invention

According to the invention, the mechanism related to neuropathy in methylmalonic acidemia has been made clear, and also, a new therapeutic drug or the like for neuropathy in organic acidemia based on this finding can be provided.

BRIEF DESCRIPTION OF DRAWINGS

FIG. 9 is a diagram showing the results of comparing and investigating the survival rates in the presence or absence of administration of a candidate drug for cAMP increase in a lethal methylmalonic acid seizure model.

MODE(S) FOR CARRYING OUT THE INVENTION

Figure 1:
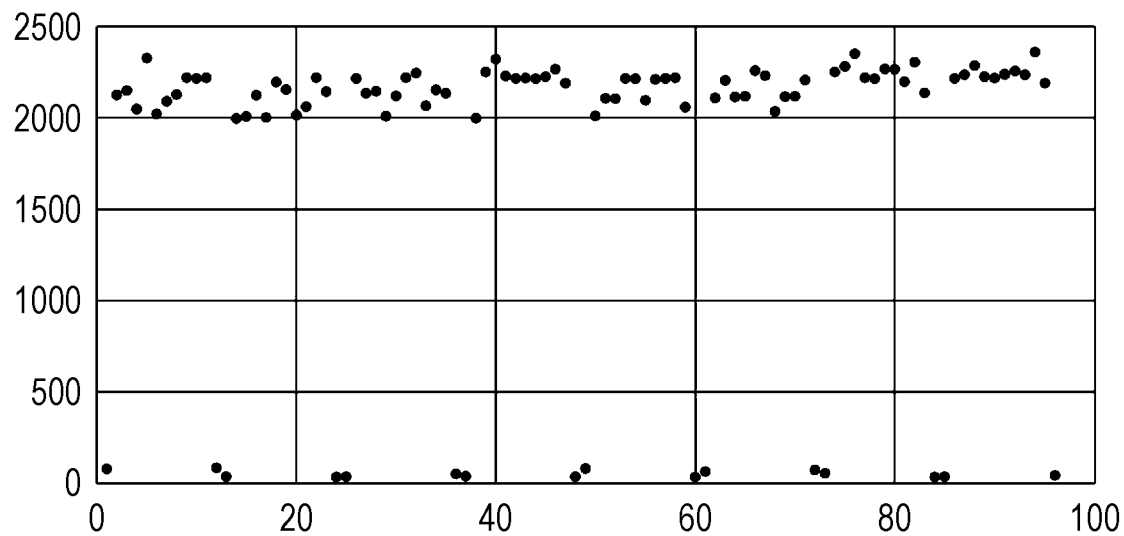
FIG. 1 is a diagram showing an investigation of the suitability of a screening experiment system using a graph.

A therapeutic drug for neuropathy and the like of the invention will be explained.

The inventors achieved, for the first time, experiment technologies for the establishment of iPS cells derived from a methylmalonic acidemia patient and establishment of a stable maintenance and culturing method using peripheral blood lymphocytes of a methylmalonic acidemia patient, and for the differentiation of methylmalonic acidemia patient-derived iPS cells into nerve cells.

The inventors made clear of the following facts by using a series of these experiment technologies. From such facts, the inventors clarified that neuropathy in organic acidemia can be treated and prevented by supplementing cAMP.

(1) The inventors discovered six compounds that bring specific recovery from neuronopathy in nerve cells derived from methylmalonic acidemia.

(2) These six compounds all had a common action of increasing intercellular cAMP or activating CREB, which is a downstream molecule.

(3) The cAMP concentration in nerve cells derived from methylmalonic acidemia was measured, and it was confirmed that the concentration was noticeably decreased compared to the concentration in nerve cells derived from a healthy person.

(4) Furthermore, since a decrease in the cAMP concentration was not seen in iPS cells derived from a methylmalonic acidemia patient, it was confirmed that this decrease in the cAMP concentration occurs as a result of differentiation into nerve cells in a methylmalonic acidemia patient.

(5) In regard to nerve cells derived from methylmalonic acidemia, it was found that when cAMP is added into the culture fluid, the cell viability and the mitochondrial functions are restored to about 90% of those of nerve cells derived from a healthy person. A similar effect was also confirmed in propionic acidemia.

(6) In regard to nerve cells derived from methylmalonic acidemia, it was confirmed that a decrease in cAMP is caused by a decrease in the activity of Adenylate cyclase. In addition, it was confirmed that the activity of CREB that uses cAMP as a substrate is not inhibited, and when Adenylate cyclase-derived cAMP is supplemented, CREB is phosphorylated. Thus, it was confirmed that a therapeutic effect is exhibited on the basis of this phosphorylation as one of the mechanisms.

(7) In an in vivo model produced through administration of methylmalonic acid, an effect of suppressing the number of times and duration of seizure caused by convulsion and an effect of increasing the survival rate were confirmed, by administering a drug that supplements cAMP to the in vivo model.

The therapeutic drug for neuropathy of the invention treats or prevents neuropathy in organic acidemia by increasing cAMP. Furthermore, as an embodiment for the treatment of neuropathy, for example, a decrease in the number of times of convulsive seizure, a decrease in the duration of convulsion, and an increase in the life prolongation effect may be mentioned.

Organic acidemia is defined as a disease in which organic acids are excessively accumulate in the living body due to abnormality of metabolic enzymes, and typical examples include methylmalonic acidemia and propionic acidemia.

The therapeutic drug for neuropathy according to the invention is defined as a compound that can achieve an increase in cAMP at a neuropathic lesion in organic acidemia, or a composition including this compound as an active ingredient. Furthermore, in view of the purpose of the invention, such a compound may be used with an intact chemical structure to achieve an increase in cAMP, or the compound can be converted to a so-called DDS-formulated compound, which receives metabolism or the like in the living body to have the structure of the compound changed, and thereby achieves an increase in cAMP at a lesion. Regarding such a compound, for example, db-cAMP, which is a compound having increased cell permeability of cAMP, can be used.

The therapeutic drug for neuropathy of the invention may further activate cAMP response element binding protein (CREB) in addition to an increase in cAMP. Since a drug that is more suitable for the mechanism of neuropathy in organic acidemia can be obtained thereby, an enhancement of the therapeutic effect for neuropathy can be expected. Examples of such a compound include Forskolin ((3R,4aR, 5S,6S,6aS,10S,10aR,10bS)-6,10,10b-trihydroxy-3,4a,7,7, 10a-pentamethyl-1-oxo-3-vinyldodecahydro-1H-benzo[f] chromen-5-yl acetate), GW9508 (3-(4-(((3-(Phenoxy) phenyl) methyl) amino) phenyl) propanoic acid), NECA (5'-N-Ethylcarboxamidoadenosine 1-(6-Amino-9H-purin-9-yl)-1-deoxy-N-ethyl-β-D-ribofuranuronamide), SKF77434 (3-allyl-1-phenyl-1,2,4,5-tetrahydro-3-benzazepine-7,8-diol), nicotinamide (pyridine-3-carboxamide), and dobutamine.

It is not necessary to particularly limit the dosage form of the therapeutic drug for neuropathy of the invention, and various dosage forms can be used. Typically, a form of a preparation for oral ingestion, such as a tablet, a capsule, or a powder, can be adopted, and in addition to that, a form of an injectable preparation, a transdermal absorption type preparation or the like can be adopted.

EXAMPLES

<<I. Experiment Materials and Experiment Method>>
<1. Method for Regulating Patient-Derived Peripheral Blood Lymphocytes>

(1) For patients, patients of organic acidemia (methylmalonic acidemia and propionic acidemia), which is the object of the present study, were selected as subjects from among ambulatory diagnostic patients of the pediatrics department of Kumamoto University Hospital. Neonatal severe cases already confirmed from enzymatic diagnoses and gene diagnoses were selected as subjects. Regarding the explanation and consent of subject patients, a written consent approved by the ethics committee in Kumamoto University Life Sciences Research Department was used.

(2) From those patients whose consent was obtained, 3 mL of patient blood was collected in the pediatrics ambulatory treatment room. This blood was aseptically transferred into a blood collecting tube (CPT) for VACUTAINER lymphocyte separation (BD catalogue No. 362753) and was moved to the fifth floor of the medical department clinical study building.

(3) The blood collecting tube for VACUTAINER lymphocyte separation (CPT) was centrifuged at 20° C. and 2,000 g/30 minutes, and a mononuclear cell layer was suctioned and then aseptically moved to into a fresh aseptic Spitz tube in a biohood.

(4) 20 mL of an aseptic phosphate buffer solution was added to the fresh aseptic Spitz tube, the mixture was stirred and centrifuged at 2,000 g/20 minutes, and then the supernatant was removed.

(5) Mononuclear cell pellets were suspended in 500 μL of BAMBANKER hRM (catalogue No. CS-07-001), and then the suspension was preserved at −80° C.

<2. Method for Establishing Patient-Derived iPS Cells>

(1) The preserved monocytic cells were stored in liquid nitrogen and then were transported to the building of Kumamoto University Institute of Molecular Embryology and Genetic.

(2) The preserved tube was melted in a constant temperature chamber at 37° C. Before the preserved tube was completely melted, 9.5 mL of D-PBS was added thereto, and the mixture was stirred.

(3) After melting, the mixture was centrifuged at 100×g/10 minutes at 10° C., and the supernatant was removed. Furthermore, 12 mL of D-PBS was added to the residue, the mixture was centrifuged at 100×g/10 minutes at 18° C., and the supernatant was removed.

(4) 5 mL of mononuclear cell medium (PBMC-CM: 100 mL of PBMC medium+100 mL of SCF stock solution+100 mL of FLT-3 stock solution+100 mL of TPO stock solution+IL6 stock solution) was added to the residue, and the residue was suspended. For the suspension, the number of live cells was counted by Trypan Blue staining.

(5) The cells were suspended using PBMC-CM medium at a proportion of $5×10^5$ cells/well, and the suspension was inoculated onto a 24-well plate at a concentration of 0.5 mL/well. After the inoculation, culture was carried out in an incubator at 37° C. and 5% $CO_2$, and from the next day, medium exchange was carried out consecutively for 3 days.

(6) Trypsin was added to a well for counting the number of cells, the cells were detached, and the number of cells was counted.

(7) A vector solution equivalent to MOI=5 was produced in PBMC-C medium, and the solution was added to each of the wells. For two days after the infection, the medium was exchanged everyday.

(8) On the second day after infection, mitomycin-treated mouse embryo fibroblasts (MEF) were inoculated onto a 6-well plate to a concentration of $1×10^6$ cells/well and were cultured at 37° C. and 5% $CO_2$.

(9) On the third day after infection, the infected cells were detached by pipetting and were superposed on MEF prepared on a 6-well plate ($1×10^5$ cells/well), and the cells were cultured in an incubator at 37° C. and 5% $CO_2$.

(10) From the fourth day to the sixth day after infection, an entire medium exchange was carried out with PBMC medium every day.

(11) On the seventh day after infection, 1 mL of the medium from 2 mL per well of the 6-well plate, and 1 mL of human iPS medium (500 mL of DMEM/F12+5 mL of NEAA+6.25 mL of 200 mM L-Glutamine+125 mL of KSR+500 µL of 0.1 M 2-Mercaptoethanol/PBS+5 ng/mL rhbFGF) was added to each well. Culture was continued in an incubator at 37° C. and 5% $CO_2$.

(12) From the eighth day to the twenty-first day after infection, an l-carnitine solution (L-cartine FF injection) was added to human iPS medium to a concentration of 500 nM, and the entire medium exchange was carried out using this FFiPS medium everyday, while observations were made twice a day.

(13) iPS colonies were picked up, and fifty clones in total were established. The patient-derived iPS cells thus established were subsequently used as disease-derived iPS cells.

(14) The clones thus established were all checked for positivity using alkaline phosphatase (AP100R-1), Nanog (SAB-103A-1), OCT4 (SAB-105A-1), TRA1-60 (SAB-100A-1), and SSEA-3 (SAB 102A-1). Furthermore, in all of the clones thus established, expression of a human iPS cell undifferentiated marker was confirmed (Human iPS cell indentification primer set ABP SC IPSHRES).

<3. Method for Maintaining and Culturing Disease-Derived iPS Cells>

The disease-specific iPS cells thus established had weak cell proliferation power and were not apt for maintenance and culture. Therefore, carnitine that has been reported to partially restore the mitochondrial functions of the present disease was added to the standard culture fluid, and culture was carried out. Thus, it was newly found that maintenance and culture were possible. Therefore, maintenance and culture were enabled using the following culturing method.

(1) According to the day of subculturing, culture of mitomycin C-treated MEF ($3×10^5$ cells/60 mm well) was carried out in advance.

(2) For disease-derived iPS cells, wells having sufficiently enlarged colonies were selected and washed two times with PBS. A cell dissociation solution (0.25 g of Trypsin, 10 mg/mL Collagenase IV, 20 mL of KSR, 100 µL of 1 M $CaCl_2$/PBS, and 70 mL of PBS) was added at a concentration of 500 µL/60 mm well, and the cells were incubated for 5 minutes in an incubator at 37° C. and 5% $CO_2$.

(3) 2 mL of a medium was added to detach the cells. 15 mL of the cell suspension was transferred into a conical tube, 5 mL of a medium was added thereto, and the mixture was centrifuged at 170×g/5 minutes.

(4) The supernatant was suctioned, and the residue was suspended in fresh FFiPS medium (carnitine-added medium). The suspension was inoculated onto MEF, and culture was carried out in an incubator at 37° C. and 5% $CO_2$.

(5) Any undifferentiated marker was checked in every five subcultures.

<4. Method for Inducing Disease-Derived iPS Cells into Neuronal Precursor Cells>

Induction of nerve cells appropriate for high-throughput drug discovery screening was attempted by various kinds of methods. As the result, it was found that the following method is suitable.

(1) For the induction of differentiation, a GIBCO Neural Induction Method was used. Regarding the initial induction, Neural Induction Medium (NIM: 490 mL of Neuralobasal Medium+10 mL of GIBCO Neural Induction Supplement) was used. Furthermore, as the maintenance culture fluid, Neural Expansion Medium (NEM: 49 mL of Neurobasal medium+49 mL of Advanced DMEN/F12+2 mL of GIBCO Neural Induction Supplement) was used.

(2) 70% to 80% confluent iPS cells were used for the induction of differentiation.

(3) The culture fluid after a lapse of 24 hours was suctioned, and cells that did not adhere were all removed. After this operation, NIM culture fluid was added thereto, and culturing was continued. The culture fluid was exchanged after every 48 hours.

(4) NSC(P) near the seventh day was subcultured as follows.

First, a culture plate coated with Geltrex matrix was prepared, and NIM was removed from the culture plate.

After the removal, the culture plate was washed with 2 mL of PBS. After washing, 1 mL of a dissociation solution was added, and the culture plate was incubated for 5 minutes.

The dissociation solution was collected in a 15-mL conical tube, washing-up of the culture plate was performed with 1 mL of PBS, and the PBS was collected into the conical tube. After the collection, the collected liquid was pipetted three times with a 5-mL pipette.

After pipetting, the cell solution was filtered through a 100-µm cell strainer (FALCON). The cells thus filtered were centrifuged for 4 minutes at 300 g. The supernatant was suctioned, the residue was suspended in PBS in an amount of 3 mL×well, and the suspension was centrifuged at 300×g for 4 minutes. Furthermore, the supernatant was suctioned, and the residue was suspended in NEM.

The cells were inoculated so as to obtain a concentration of from $2\times10^5$ cells/mL to $4\times10^5$ cells/mL. Furthermore, Y27632 was added to the cell suspension to a concentration of 5 µM.

After 24 hours, the culture fluid was removed, and the culture fluid was exchanged with fresh NEM culture fluid.

(5) For the subsequent screening process, this Neural Progenitor cells (NPCs) were used.

<<II. Establishment of Screening System>>

<1. Drug Screening Candidate Compound List>

In the present screening experiment, a compound library (trade name: SIGMA PETIT SCREENING 2014), commercially available from Sigma-Aldrich Corporation, which consists of 440 kinds of compounds, the operating mechanisms of which have been identified, was used. The compound library used for the present Experiment Example is shown in the following table.

TABLE 1

| PETIT SCREENING 2014 | Series | CAT. NO. (compound list) | Number of compounds |
|---|---|---|---|
| Naturally sorted active substance library (old version) | IV | S990043-NAT4 | 80 |
| Cancer-suppressing compound library | I | S990043-ATU1 | 80 |
|  | II | S990043-ATU2 | 80 |
| Agonist/activated factor library | I | S990043-AG01 | 80 |
|  | II | S990043-AG02 | 40 |
| Inhibitor library | IV | S990043-INH4 | 80 |
|  | V | S990043-INH5 | 80 |
|  | VI | S990043-INH6 | 80 |
|  | VII | S990043-INH7 | 80 |

<2. Screening Method>

[Screening System 1: Screening System for Compounds that Reduce Exogenic Methylmalonic Acid and Propionic Acid Toxicity Using Skin Fibroblasts]

(1) Fibroblasts derived from a healthy child and a patient were precultured. The cultured cells were inoculated, in a 80% confluent state, onto a 96-well collagen-coated dish at a proportion of $5\times10^3$ cells/well. After the inoculation, the cells were precultured in an incubator at 5% $CO_2$ for 24 hours.

(2) A methylmalonic acid solution at a concentration of 200 µM was added to DMEM/F12/10% FBS medium, and culturing was carried out. Regarding propionic acid, a similar operation was carried out by adjusting the concentration to 400 µM.

(3) Each compound was added to each well at a concentration of 5 µM. As an object of comparison, DMSO was added.

(4) After 24 hours, measurement of the light absorbance through a 450-nm filter was carried out using the WST-8 method.

[Screening System: Screening System for Compounds that Ameliorate Endogenic Metabolic Disturbance Using Skin Fibroblasts]

(1) Screening was carried out by a method similar to that of the screening system 1. That is, fibroblasts derived from a healthy child and a patient were precultured. The cultured cells were inoculated, in a 80% confluent state, onto a 96-well collagen-coated dish at a proportion of $5\times10^3$ cells/well. After the inoculation, the cells were precultured in an incubator at 5% $CO_2$ for 24 hours.

(2) Each compound was added to each well at a concentration of 5 µM.

(3) After 24 hours, measurement of the light absorbance through a 450-nm filter was carried out using the WST-8 method.

[Screening System 3: Screening System for Therapeutic Compounds that Reduce Exogenic Neurotoxicity Using Neuronal Precursor Cells (NPCs) Induced from Disease-Specific iPS Cells]

(1) NPCs were cultured using the above-described differentiation induction method (I-3).

(2) NPCs were inoculated onto a 96-well geltrex-coated dish (GIBCO) so as to obtain a concentration of $1\times10^5$ cells/well. After the inoculation, culturing was carried out in an incubator at 5% $CO_2$ at 37° C. for 24 hours.

(3) After 24 hours, methylmalonic acid was added to the culture fluid so as to obtain a concentration of 100 µM. In the case of propionic acid, the acid was added to the culture fluid supernatant so as to obtain a concentration of 200 µM.

(4) Each compound was added to each well so as to obtain a concentration of 5 µM. As an object of comparison, DMSO was added.

(5) After 24 hours, measurement of the light absorbance was carried out using the WST-8 method.

[Screening System 4: Screening System for Compounds that Ameliorate Endogenic Metabolic Function Disturbance Using Neuronal Precursor Cells (NPCs) Induced from Disease-Specific iPS Cells]

(1) Screening was carried out by a method similar to that for the screening system 3. That is, NPCs were cultured using the above-described differentiation induction method (I-3).

(2) NPCs were inoculated onto a 96-well geltrex-coated dish (GIBCO) so as to obtain a concentration of $1\times10^5$ cells/well. After the inoculation, culturing was carried out in an incubator at 5% $CO_2$ at 37° C. for 24 hours.

(3) Each compound was added to each well so as to obtain a concentration of 5 µM. As an object of comparison, DMSO was added.

(4) After 24 hours, measurement of the light absorbance was carried out using the WST-8 method.

<3. Validation Results for Screening Systems>

(1) Validity of the present screening systems was verified.

(2) In the screening experiment, an investigation is carried out using a 96-well plate, and the purpose of the screening experiment is to screen a compound that reduces organic acid toxicity. From this point of view, the 0% control of the first and twelfth wells were made into wells to which methylmalonic acid (or propionic acid) was not added, and the second to the eleventh wells were used for a toxicity test. The results are shown in Table 2 and FIG. 1.

(3) From Table 2, the following were obtained: CV value <10%, S/B ratio >3, S/N ratio >80, and Z-factor >0.5. Thus, the screening systems were considered as adequate screening systems.

(4) Therefore, the present screening systems were used for the screening of compounds in the subsequent Experiment Examples, as appropriate experiment systems.

TABLE 2

|   | 1 | 2 | 3 | 4 | 5 | 6 | 7 | 8 | 9 | 10 | 11 | 12 |
|---|---|---|---|---|---|---|---|---|---|----|----|----|
| A | 359 | 2125 | 2149 | 2047 | 2327 | 2021 | 2089 | 2126 | 2219 | 2216 | 2220 | 427 |
| B | 441 | 1995 | 2006 | 2123 | 2002 | 2195 | 2155 | 2014 | 2061 | 2219 | 2144 | 415 |
| C | 401 | 2215 | 2135 | 2145 | 2008 | 2120 | 2220 | 2245 | 2065 | 2152 | 2135 | 398 |
| D | 379 | 1998 | 2250 | 2320 | 2228 | 2215 | 2218 | 2214 | 2225 | 2265 | 2189 | 389 |
| E | 405 | 2010 | 2106 | 2105 | 2215 | 2218 | 2096 | 2210 | 2216 | 2220 | 2058 | 389 |
| F | 411 | 2106 | 2205 | 2114 | 2118 | 2258 | 2230 | 2035 | 2115 | 2118 | 2207 | 419 |
| G | 423 | 2250 | 2280 | 2350 | 2220 | 2214 | 2268 | 2265 | 2197 | 2305 | 2136 | 413 |
| H | 415 | 2215 | 2265 | 2285 | 2224 | 2218 | 2237 | 2257 | 2286 | 2360 | 2189 | 367 |
| Average | 404 | 2115 | 2171 | 2186 | 2168 | 2182 | 2189 | 2171 | 2167 | 2232 | 2160 | 402 |
| SD | 25.52 | 105.21 | 89.92 | 114.25 | 115.01 | 75.67 | 67.44 | 160.18 | 74.14 | 78.16 | 52.58 | 19.94 |
| | Z-factor | 0.82 | | CV | 4.0814 | | S/B | 5.4061 | | S/N | 88.862 | |

<<III. Experiment Example>>
<Experiment Example 1. Influence of Various Compounds on Neuronopathy>

(1) An investigation was conducted using the various compounds shown in Table 1 to find what influence the various compounds would have on neuronopathy.

(2) The results are presented in Table 3.

To explain an outline of Table 3, a statistical treatment was carried out using a heat map, and an average of the negative controls (first row and twelfth row of 96 wells) was determined and designated as −1, while an average of the positive controls (not shown in the diagram) was determined and designated as +1. Each of the drug data was subjected to normalization into a value between −1 and +1, and the experiment was repeated three or more times. Drug data exhibiting high reproducibility and efficacy are surrounded by ○.

From these results, in cells derived from a patient, six kinds of compounds enabled recovery from neuronopathy in a disease-specific manner. These compounds were Forskolin, GW9508, NECA, SKF77434, nicotinamide, and dobutamine.

(3) Furthermore, it was found that all of these compounds have a common action of increasing intracellular cAMP and having an effect of activating CREB, which is a downstream key regulator.

TABLE 3

|   | 1 | 2 | 3 | 4 | 5 | 6 | 7 | 8 | 9 | 10 | 11 | 12 |
|---|---|---|---|---|---|---|---|---|---|----|----|----|
| *Agonist I* | | | | | | | | | | | | |
| A | 0.172 | (0.227) | 0.159 | 0.158 | 0.147 | 0.148 | 0.15 | 0.159 | 0.164 | 0.154 | 0.159 | 0.171 |
| B | 0.16 | 0.149 | 0.179 | 0.156 | 0.145 | 0.147 | 0.156 | 0.148 | 0.153 | 0.151 | 0.153 | 0.172 |
| C | 0.172 | 0.152 | 0.158 | 0.153 | 0.137 | 0.144 | 0.148 | 0.149 | 0.152 | 0.151 | 0.157 | 0.172 |
| D | 0.161 | 0.181 | 0.178 | 0.166 | (0.215) | 0.149 | 0.145 | 0.15 | 0.152 | 0.152 | 0.152 | 0.156 |
| E | 0.141 | 0.153 | 0.163 | 0.155 | 0.148 | 0.145 | 0.146 | 0.145 | 0.151 | 0.152 | 0.152 | 0.165 |
| F | 0.132 | 0.137 | 0.138 | 0.115 | 0.132 | (0.201) | 0.137 | 0.155 | 0.148 | 0.141 | 0.149 | 0.167 |
| G | 0.122 | 0.162 | 0.179 | 0.113 | 0.153 | 0.144 | 0.146 | 0.146 | 0.15 | 0.15 | 0.152 | 0.155 |
| H | 0.208 | 0.296 | 0.19 | (0.258) | 0.157 | 0.27 | 0.164 | 0.156 | 0.146 | 0.157 | 0.156 | 0.2 |
| *Agonist I* | | | | | | | | | | | | |
| A | 0.214 | (0.361) | 0.24 | 0.241 | 0.235 | 0.237 | 0.239 | 0.25 | 0.246 | 0.243 | 0.249 | 0.245 |
| B | 0.231 | 0.237 | 0.248 | 0.233 | 0.234 | 0.243 | 0.238 | 0.236 | 0.239 | 0.246 | 0.236 | 0.239 |
| C | 0.229 | 0.109 | 0.226 | 0.227 | 0.209 | 0.236 | 0.233 | 0.243 | 0.237 | 0.242 | 0.239 | 0.236 |
| D | 0.208 | 0.219 | 0.237 | 0.24 | (0.336) | 0.235 | 0.236 | 0.243 | 0.223 | 0.24 | 0.238 | 0.237 |
| E | 0.232 | 0.236 | 0.213 | 0.232 | 0.239 | 0.237 | 0.235 | 0.24 | 0.238 | 0.242 | 0.224 | 0.22 |
| F | 0.213 | 0.197 | 0.175 | 0.2 | 0.219 | (0.33) | 0.198 | 0.229 | 0.205 | 0.219 | 0.219 | 0.173 |
| G | 0.238 | 0.24 | 0.248 | 0.222 | 0.231 | 0.228 | 0.24 | 0.23 | 0.233 | 0.238 | 0.218 | 0.229 |
| H | 0.247 | 0.245 | 0.234 | (0.261) | 0.235 | 0.239 | 0.25 | 0.237 | 0.236 | 0.245 | 0.232 | 0.236 |
| *Agonist II* | | | | | | | | | | | | |
| A | 0.171 | 0.171 | 0.231 | 0.157 | 0.205 | 0.24 | 0.162 | 0.158 | 0.153 | 0.161 | 0.168 | 0.169 |
| B | 0.168 | 0.178 | 0.159 | 0.15 | 0.146 | 0.146 | 0.153 | 0.159 | 0.151 | 0.153 | 0.165 | 0.164 |
| C | 0.171 | 0.162 | 0.157 | 0.154 | 0.16 | 0.16 | 0.152 | 0.165 | 0.151 | 0.154 | 0.161 | 0.165 |
| D | 0.168 | 0.159 | 0.156 | 0.159 | 0.152 | 0.152 | 0.154 | 0.16 | 0.152 | 0.153 | 0.162 | 0.162 |
| E | 0.173 | 0.165 | 0.151 | 0.163 | 0.156 | 0.156 | 0.152 | 0.157 | 0.147 | 0.15 | 0.155 | 0.157 |
| F | 0.157 | 0.164 | 0.157 | 0.145 | 0.144 | 0.144 | 0.148 | 0.157 | 0.147 | 0.152 | 0.163 | 0.154 |
| G | 0.18 | 0.197 | 0.157 | (0.197 / 0.227) | 0.156 | 0.156 | 0.153 | 0.153 | 0.149 | 0.15 | 0.163 | 0.159 |
| H | 0.165 | 0.267 | 0.3 | | 0.166 | 0.166 | 0.162 | 0.165 | 0.165 | 0.204 | 0.153 | 0.166 |
| *Agonist II* | | | | | | | | | | | | |
| A | 0.247 | 0.244 | 0.154 | 0.243 | 0.248 | 0.259 | 0.254 | 0.25 | 0.254 | 0.212 | 0.212 | 0.261 |
| B | 0.243 | 0.243 | 0.245 | 0.234 | 0.244 | 0.248 | 0.247 | 0.245 | 0.245 | 0.23 | 0.23 | 0.248 |
| C | 0.238 | 0.216 | 0.223 | 0.243 | 0.249 | 0.228 | 0.242 | 0.239 | 0.137 | 0.241 | 0.231 | 0.253 |

TABLE 3-continued

|   | 1 | 2 | 3 | 4 | 5 | 6 | 7 | 8 | 9 | 10 | 11 | 12 |
|---|---|---|---|---|---|---|---|---|---|----|----|----|
| D | 0.231 | 0.218 | 0.24 | 0.235 | 0.239 | 0.245 | 0.242 | 0.197 | 0.233 | 0.234 | 0.234 | 0.249 |
| E | 0.239 | 0.193 | 0.241 | 0.235 | 0.241 | 0.193 | 0.225 | 0.236 | 0.223 | 0.231 | 0.231 | 0.256 |
| F | 0.229 | 0.171 | 0.276 | 0.22 | 0.21 | 0.222 | 0.226 | 0.193 | 0.188 | 0.209 | 0.209 | 0.221 |
| G | 0.236 | 0.276 | 0.245 | 0.325 | 0.247 | 0.234 | 0.234 | 0.231 | 0.229 | 0.238 | 0.238 | 0.244 |
| H | 0.24 | 0.24 | 0.245 | 0.272 | 0.253 | 0.228 | 0.237 | 0.231 | 0.253 | 0.237 | 0.237 | 0.228 |

<Experiment Example 2. Secondary Screening Using Patient-Derived Neuronal Precursor Cells>

(1) From the results of Experiment Example 1, a possibility that cAMP would exhibit a therapeutic effect on methylmalonic acidemia was suggested. From this point of view, an investigation was conducted to see whether cAMP has a protective effect on methylmalonic acidemia patient-derived neuronal precursor cells (hereinafter, MMA patient-derived neuronal precursor cells).

(2) MMA patient-derived neuronal precursor cells were cultured for 24 hours on a 96-well plate (Gelatin-coated) at a concentration of $1 \times 10^4$ cells/well, db-cAMP was added at a concentration of 0, 500 nM, 1 μM, 10 μM, or 500 μM, and the cells were cultured for 24 hours. Subsequently, the light absorbance was measured by the WST8 method.

Figure 2:
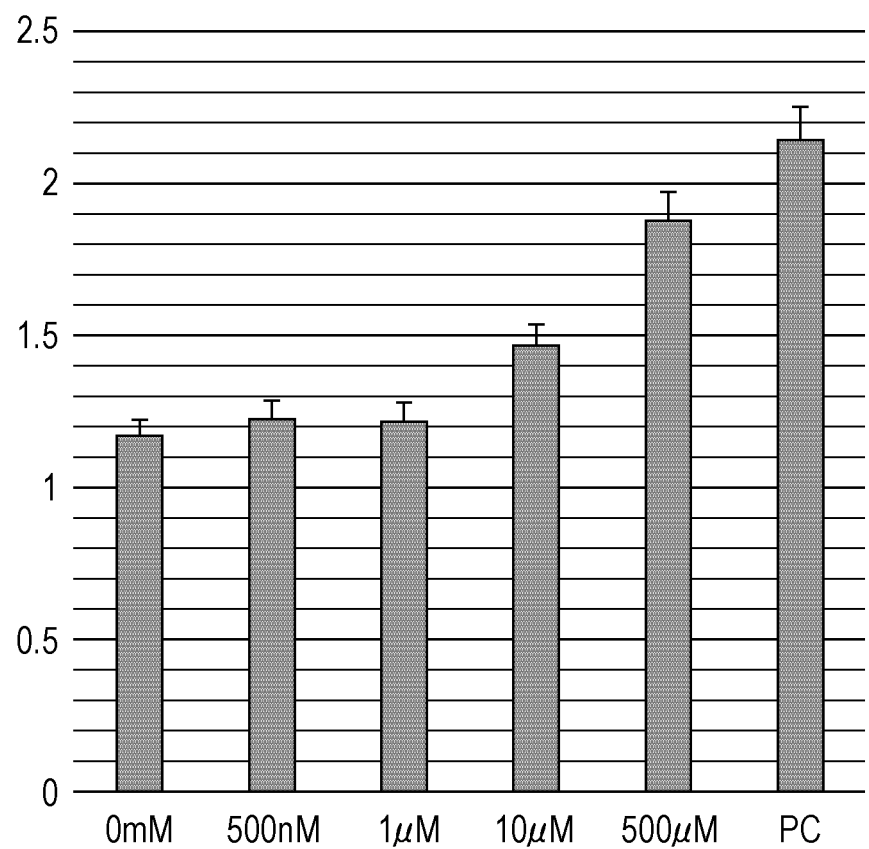
FIG. 2 shows a protective action of dibutyl-cAMP for neuronal precursor cells derived from a methylmalonic acidemia patient.

(3) The results are shown in FIG. 2. A cell protecting effect was recognized proportionally to the concentration of cAMP added to the culture supernatant. It was found that this effect restores to about 90% of a normal subject at the maximum.

<Experiment Example 3. Experiment for cAMP Comparison Between Patient-Derived Nerve Cells and Normal Nerve Cells>

(1) From the results of Experiment Example 1 and Experiment Example 2, a possibility that a disease-specific decrease in the intracellular cAMP concentration may be a disease condition of the present disease. Therefore, for the purpose of investigating whether a cell protective effect of cAMP on nerve cells derived from methylmalonic acidemia is specific to methylmalonic acidemia, the intracellular cAMP concentration was measured.

(2) For the measurement of the intracellular cAMP concentration, a cAMP complete ELISA kit (ADI-900-163) of Enzo Co., Ltd. was used.

(3) On the occasion of performing measurement, a pre-treatment of cells was carried out.

Cells were detached from the culture plate, the number of cells was counted, and centrifugation was performed. After the centrifugation, the supernatant was suctioned, and the residue was suspended in a 0.1 M HCl solution at a concentration of $1 \times 10^6$/cells/mL. In the case of cells with a known cell count, a series of these operations was omitted, and 0.1 M HCl was introduced directly onto the culture plate while the cells were adhered.

After suspending, the suspension was incubated at room temperature for 10 minutes and then was centrifuged at 600 g/5 minutes. This supernatant was preserved at −80° until the measurement of cAMP was performed.

(4) For the measurement, measurement was carried out through a series of the following processes.

A neutralizing liquid (Neutralizing reagent) was introduced in an amount of 50 μL into wells other than total activity (TA) and blanks.

Subsequently, 100 μL of a standard diluent was added to non-specific binding (NBS) and B0 (0 pmol/mL standard). Furthermore, 50 μL of a standard diluent was added to the wells of NBS. Furthermore, 100 μL each of reference dilution series from #1 to #5 was added.

A sample was added to each well in an amount of 100 μL each.

A blue conjugate solution was introduced in an amount of 50 μL each into wells other than total activity (TA) and blanks.

Yellow (yellow antibody) was introduced in an amount of 50 μL each into wells other than blanks, TA, and NSB (blank: transparent, TA: transparent, NSB: blue, sample and standard were green).

The plate was sealed and was incubated for 2 hours at room temperature in a shaker.

After incubation, all wells were suctioned, and then the plate was washed three times in total with 400 μL of a washing solution. Finally, the plate was dried on a KIMTOWEL.

5 μL of a blue (blue conjugate) solution was added to the wells of TA.

200 μL of a substrate solution was added, the plate was left to stand for one hour at room temperature, and then 50 μL of a stop solution was added thereto. The light absorbance at 405 nm was measured.

Figure 3:
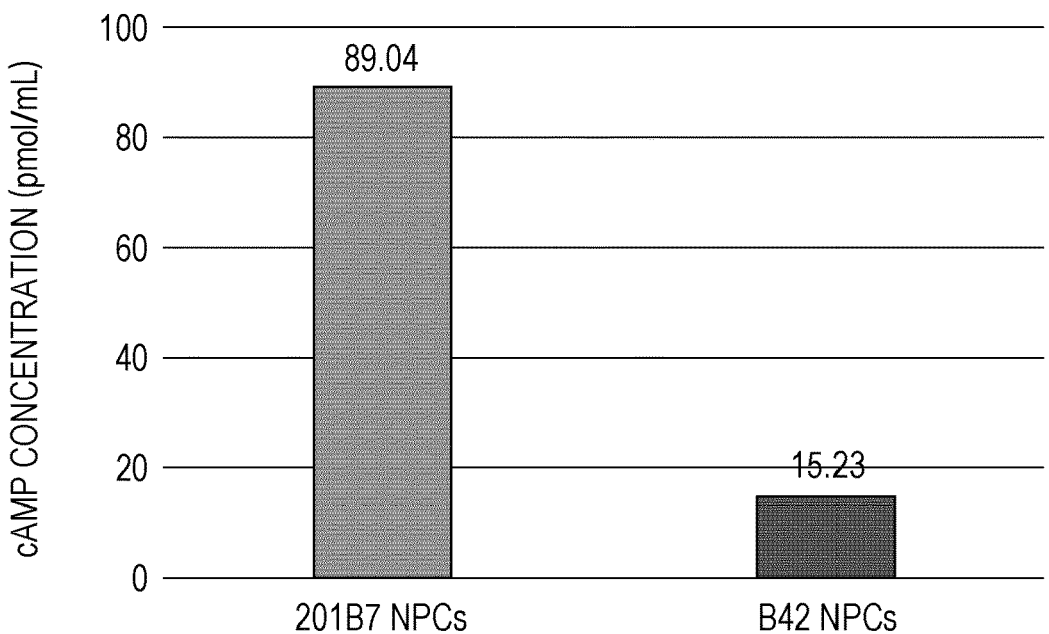
FIG. 3 is a diagram showing a comparison of the intracellular cAMP concentrations in normal iPS cell-derived neuronal precursor cells (201B7 NPCs) and methylmalonic acid patient iPS cell-derived neuronal precursor cells (B47 NPCs).

(5) The results are presented in FIG. 3. In FIG. 3, 201B7 NPCs represent the intracellular cAMP concentration of normal iPS cell-derived neuronal precursor cells, and B42NPCs represent the intracellular cAMP concentration of methylmalonic acid patient iPS cell-derived neuronal precursor cells.

(6) A comparison between the cAMP concentration in the methylmalonic acidemia-derived nerve cells and the cAMP concentration in the normal nerve cells was carried out, and as a result, it was found that the cAMP concentration was noticeably decreased in the methylmalonic acidemia-derived nerve cells.

(7) As a result of a series of experiments carried out thus far, it was found that the cAMP concentration was decreased in the methylmalonic acidemia patient-derived neuronal precursor cells, and the cellular functions were restored by replenishing cAMP. This suggests a possibility that a decrease in cAMP represents a disease state specific to the present disease, and a treatment of replenishing cAMP may become a fundamental treatment.

<Experiment Example 4. cAMP Production Ability Test for Methylmalonic Acidemia Patient>

(1) The cAMP production ability in methylmalonic acidemia patient-derived neuronal precursor cells was measured.

(2) Specifically, Neural Progenitor cells (NeuP) were induced from normal iPS cells and MMA-derived iPS cells. To these cells, Forskolin (FSK) was added at a concentration of 10 μmol/l, and the intracellular cAMP concentration after 24 hours was measured.

Figure 4:
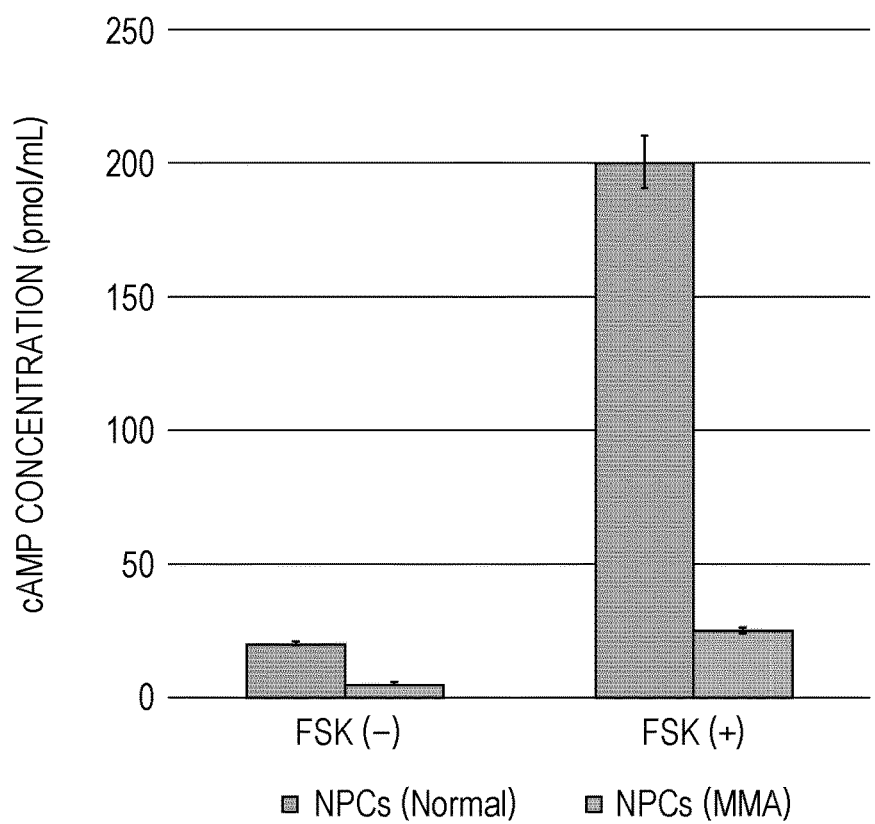
FIG. 4 is a diagram showing a comparison of the intracellular cAMP production abilities depending on the addition of Forskolin.

(3) The results are presented in FIG. 4. As a result of the investigation, in methylmalonic acidemia-derived NPCs, a decrease in reactivity to Forskolin was recognized, and it was suggested that the cAMP production ability was deteriorated.

<Experiment 5. Signal Inhibition Test>

(1) Signal transduction involving cAMP is well known, and an inhibition experiment of using a library of drugs that inhibit these pathways was carried out. Raw data of the results are presented in Table 4.

(2) As the result, the following were found.
A cAMP production inhibitor aggravated cell damage of methylmalonic acid.
A cAMP decomposition inhibitor ameliorated cell damage of methylmalonic acid.
ERK inhibition aggravated cell damage of methylmalonic acid.
CREB inhibition ameliorated cell damage of methylmalonic acid.

(3) Furthermore, from an experiment of using agonists and inhibitors, the following were found.
When ERK is activated, and CREB is inhibited, cytotoxicity is exacerbated.
Even if cAMP is added in a state of having CREB inhibited, a cell protecting effect is not obtained.

(4) From the above results, it was found that cell damage (toxicity) of methylmalonic acid is caused by decreased production of intracellular cAMP, this is cellular dysfunction caused by chronic deterioration of the production ability of cAMP, and a therapeutic effect of db-cAMP is exhibited through CREB.

(4) From these, it was found that a decrease in the cAMP production caused by MMA addition is attributed to a decrease in the activity of Adenylate cyclase.

From the above results, the inventors found that cell damage (toxicity) of methylmalonic acid is caused as the intracellular cAMP concentration is decreased by a decrease in the activity of Adenylate cyclase. In addition, it was found that such mechanism causes cellular dysfunction caused by a decrease in the chronic production ability of cAMP, and the therapeutic effect of cAMP is exhibited through CREB.

<Experiment 7. In Vivo Test Using Convulsion as Index>

A methylmalonic acid-administered mouse was used as a simplified neuropathy model for methylmalonic acidemia. In regard to this model, convulsion caused by administration of methylmalonic acid was used as an index, and an evaluation of the candidate drug was carried out.

1. 1 mg/kg/dosel of a methylmalonic acid solution was subcutaneously administered to four-week old C57BL/6J mice once a day, and evaluation was performed in the sixth week of age.

2. Subcutaneous administration of db-cAMP (30 mg/kg/dose) and a PDE4 inhibitor (1 mg/kg/day) as candidate drugs was performed, and the numbers of times of convulsive seizure and the total durations before and after the administration were measured. Thus, an investigation of comparison was carried out. Meanwhile, before the administration, measurement as a control was carried out for 30 minutes, and after the administration, measurement was carried out three times for 30 minutes each time, from 15

TABLE 4

|   | 1 | 2 | 3 | 4 | 5 | 6 | 7 | 8 | 9 | 10 | 11 | 12 |
|---|---|---|---|---|---|---|---|---|---|----|----|----|
| A | 1.084 | 0.997 | 0.200 | 1.005 | 1.063 | 0.844 | 0.310 | 1.034 | 0.964 | 1.110 | 1.066 | 1.264 |
| B | 1.162 | 1.018 | 0.905 | 0.882 | 0.988 | 0.982 | 0.221 | 1.007 | 1.034 | 0.890 | 0.961 | 1.307 |
| C | 1.027 | 1.020 | 0.904 | 0.793 | 0.839 | 0.869 | 0.910 | 0.932 | 0.787 | 0.993 | 5.818 | 1.258 |
| D | 1.100 | 0.949 | 0.819 | 1.021 | 0.846 | 0.187 | 0.889 | 0.854 | 0.547 | 1.609 | 1.087 | 1.263 |
| E | 1.078 | 0.982 | 0.878 | 0.892 | 0.161 | 0.870 | 0.869 | 0.867 | 0.747 | 0.950 | 0.987 | 1.207 |
| F | 1.080 | 0.862 | 0.182 | 0.887 | 0.826 | 1.081 | 0.938 | 0.914 | 1.075 | 1.607 | 1.186 | 1.175 |
| G | 0.115 | 1.134 | 0.896 | 1.095 | 0.959 | 0.931 | 1.037 | 0.336 | 0.150 | 0.809 | 1.185 | 1.288 |
| H | 1.047 | 1.065 | 0.119 | 0.845 | 1.038 | 0.999 | 1.021 | 1.136 | 1.008 | 1.078 | 0.857 | 1.441 |

<Experiment 6. Experiment on Adenylate Cyclase Inhibition by Methylmalonic Acid> cAMP is produced from ATP by Adenylate cyclase. From this point of view, an investigation was conducted on whether methylmalonic acid would inhibit Adenylate cyclase.

1. With regard to methylmalonic acidemia patient iPS cell-derived neuronal precursor cells (B42NPCs), culturing was carried out with a culture fluid to which methylmalonic acid had been added to a final concentration of 50 µM or 100 µM, and the cAMP concentration after 24 hours was measured.

Figure 5:
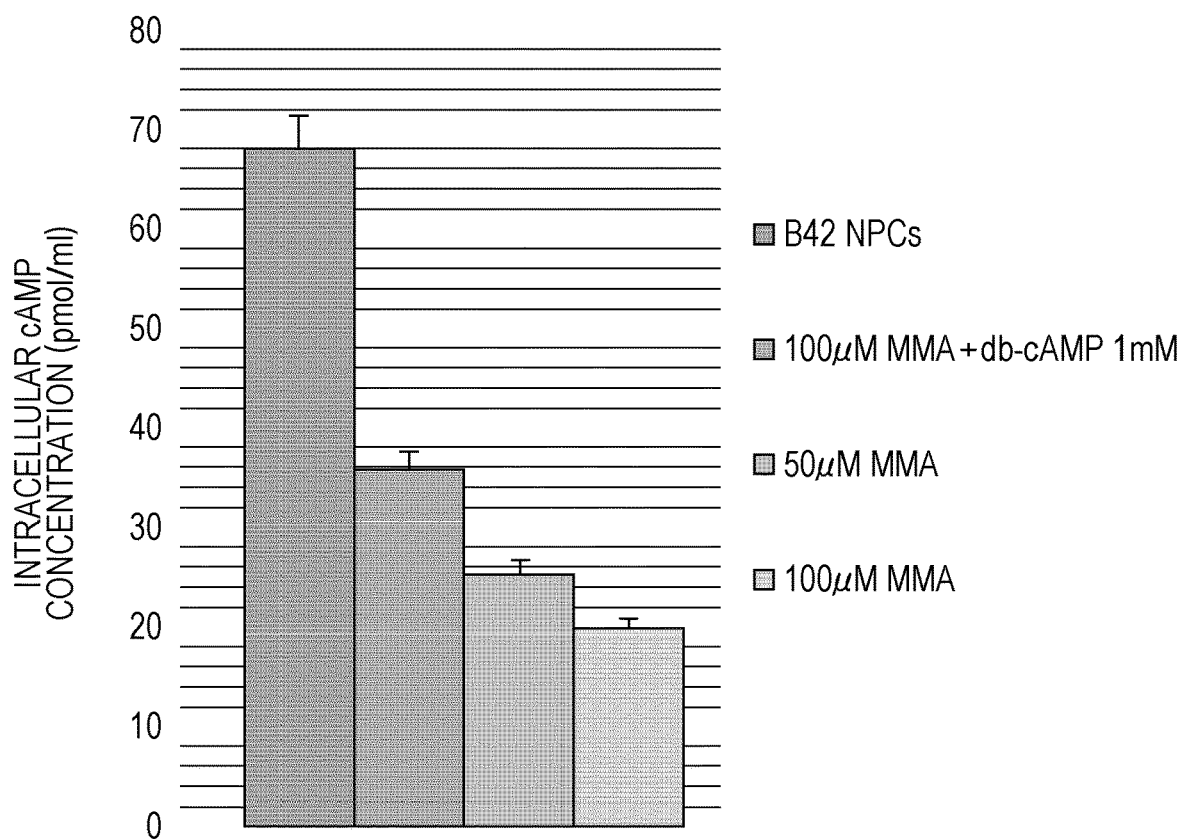
FIG. 5 is a diagram showing an investigation of the influence of the addition of methylmalonic acid on the intracellular cAMP concentration in methylmalonic acid patient iPS cell-derived neuronal precursor cells (B42 NPCs).
Figure 6:
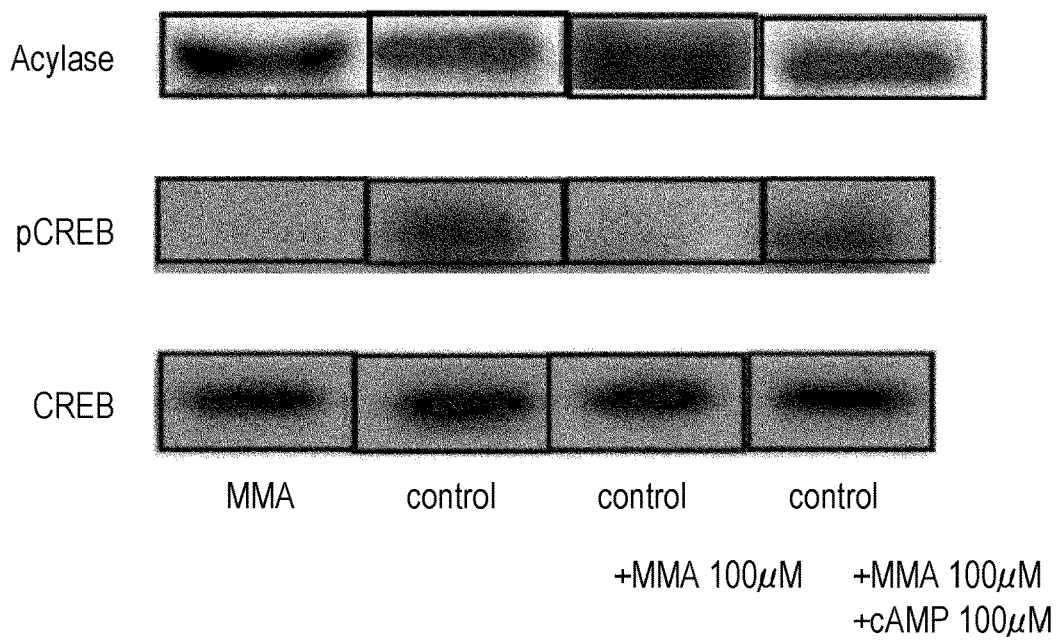
FIG. 6 is a diagram showing an investigation of the amount of expression of various proteins under various conditions in methylmalonic acid patient iPS cell-derived neuronal precursor cells (B42 NPCs).

2. The results are shown in FIG. 5 and FIG. 6. Meanwhile, the protein expression analysis shown in FIG. 6 was carried out based on the existing Western Blotting method.

(1) It was found that as the methylmalonic acid concentration in the culture fluid is higher, the cAMP production power is decreased (FIG. 5).

(2) On the other hand, the total amounts of protein expression of Adenylate cyclase and CREB were constant irrespective of the presence or absence of the addition of methylmalonic acid (FIG. 6).

(3) Furthermore, it was found that even in the presence of MMA, in a case in which cAMP was added, the expression of phosphorylated CREB was increased, and phosphorylation (activation) of CREB was not inhibited.

minutes to 45 minutes, from 55 minutes to 85 minutes, and from 90 minutes to 120 minutes.

Figure 7:
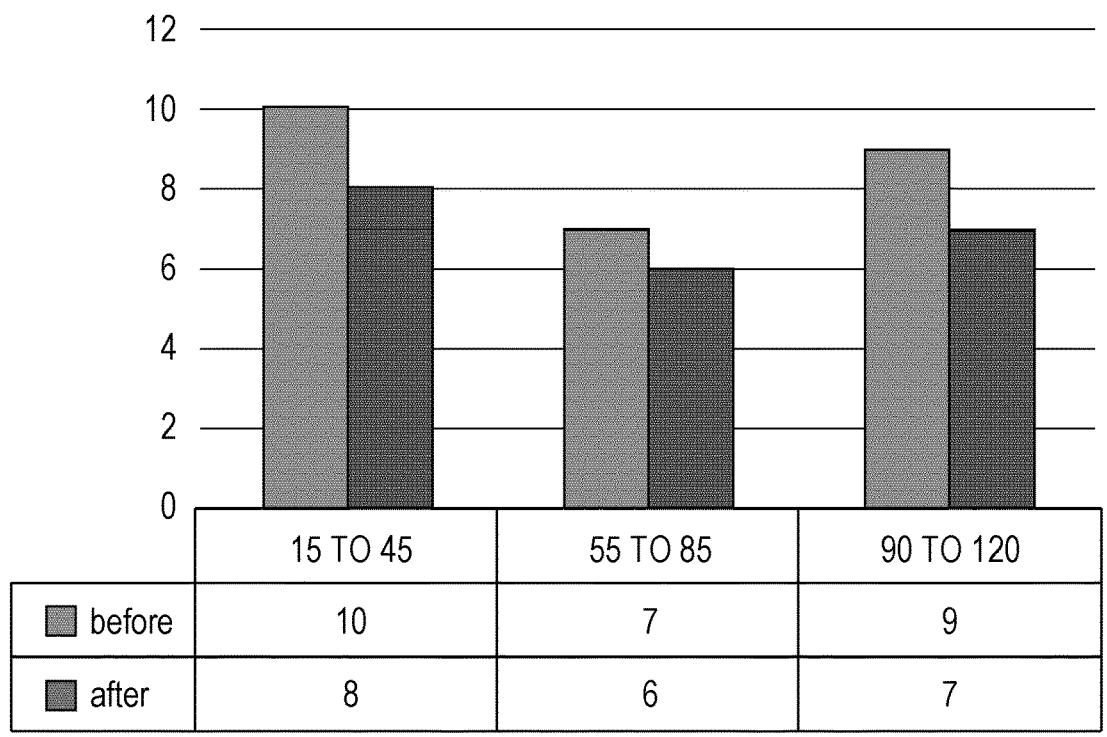
FIG. 7 is a diagram showing the results of comparing and investigating the numbers of times of seizure measured before and after the administration of a candidate drug for cAMP increase in a simplified neuropathy model of methylmalonic acidemia.
Figure 8:
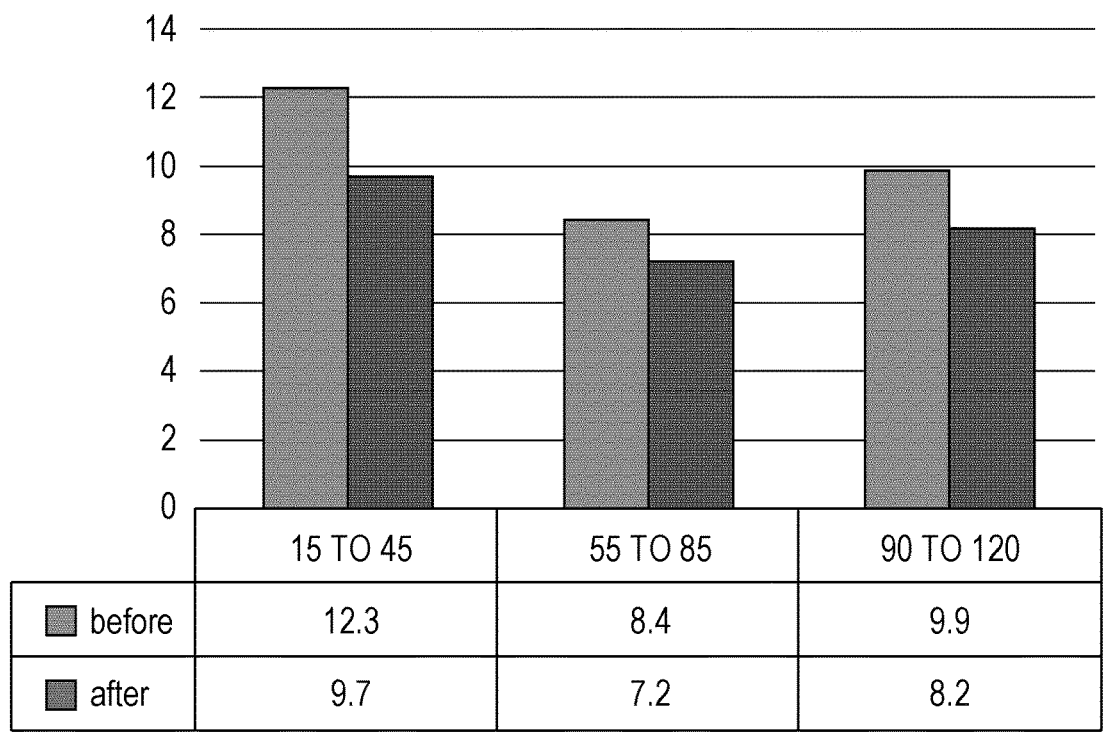
FIG. 8 is a diagram showing the results of comparing and investigating the total durations of seizure measured before and after the administration of a candidate drug for cAMP increase in a simplified neuropathy model of methylmalonic acidemia.

3. The results are presented in FIGS. 7 and 8.

(1) The number of times of seizure was decreased in all of the measurement sections, through administration of the candidate drugs.

(2) Similarly, the total duration was shortened in all of the measurement sections, through administration of the candidate drugs.

4. From these results, it was found that even in an in vivo condition, neuropathy in methylmalonic acidemia is suppressed by promoting an increase in the cAMP concentration.

<Experiment 8. In Vivo Test Using Survival Rate as Index>

An evaluation of administration of candidate drugs was carried out using the survival rate as an index, using a lethal methylmalonic acid seizure model.

1. A 500 µM methylmalonic acid solution was intraperitoneally administered to eight-week old C57BL/6J mice at a dose of 20 ml/kg, and thus a lethal methylmalonic acid seizure model was produced.

2. After one day, after two days, and after three days from the administration of methylmalonic acid, subcutaneous administration of db-cAMP (10 µg/kg/dose) as a candidate drug was performed, and a comparison of the survival rates in an administered group and a non-administered group was carried out.

3. The results are presented in FIG. 9.

(1) In the non-administered group, the survival rate was 35.3% one day after the administration of methylmalonic acid, and the survival rate was 14.7% after two days.

(2) On the other hand, in the administered group, the survival rate was 85.0% one day after the administration of methylmalonic acid, and the survival rate was 75.0% after two days. The administered group exhibited a significantly high survival rate compared to the non-administered group ($p<0.001$).

4. From these results, it was found that the vital prognosis based on seizure originating from methylmalonic acidemia is markedly ameliorated by promoting the increase in the cAMP concentration through the administration of db-cAMP.

The invention claimed is:

1. A method for treating neuropathy in organic acidemia, comprising increasing cAMP in nerve cells of a patient of the organic acidemia, wherein the organic acidemia is selected from a group consisting of methylmalonic acidemia and propionic acidemia, and wherein the method further comprises administering, to the patient of the organic acidemia, one selected from a group consisting of Forskolin ((3R,4aR,5S,6S,6aS,10S,10aR,10bS)-6,10,10b-trihydroxy-3,4a,7,7,10a-pentamethyl-1-oxo-3-vinyldodecahydro-1H-benzo[f]chromen-5-yl acetate), GW9508 (3-(4-(((3-(Phenoxy)phenyl) methyl) amino) phenyl) propanoic acid), NECA (5'-N-Ethylcarboxamidoadenosine 1-(6-Amino-9H-purin-9-yl)-1-deoxy-N-ethyl-β-D-ribofuranuronamide), SKF77434 (3-allyl-1-phenyl-1,2,4,5-tetrahydro-3-benzazepine-7,8-diol), dobutamine and db-cAMP.

2. The method according to claim 1, further comprising activating CREB in the nerve cells of the patient of the organic acidemia.

3. The method according to claim 1, the increase in cAMP is achieved by suppressing a decrease in an activity of Adenylate cyclase.

4. The method according to claim 1, wherein the organic acidemia is methylmalonic acidemia.

* * * * *